United States Patent
Hoagland et al.

(10) Patent No.: US 8,636,883 B2
(45) Date of Patent: Jan. 28, 2014

(54) MONITORABLE HYDROGEN SENSOR SYSTEM

(75) Inventors: William Hoagland, Boulder, CO (US); David K. Benson, Golden, CO (US)

(73) Assignee: Element One, Inc., Boulder, CO (US)

( * ) Notice: Subject to any disclaimer, the term of this patent is extended or adjusted under 35 U.S.C. 154(b) by 1087 days.

(21) Appl. No.: 11/685,179

(22) Filed: Mar. 12, 2007

(65) Prior Publication Data

US 2007/0209937 A1    Sep. 13, 2007

Related U.S. Application Data

(60) Provisional application No. 60/781,419, filed on Mar. 10, 2006.

(51) Int. Cl.
*G01N 27/26* (2006.01)

(52) U.S. Cl.
USPC ........... 204/400; 204/402; 204/406; 204/407; 422/82.02

(58) Field of Classification Search
USPC .............. 422/82.02; 204/400–402, 406–407, 204/431–432
See application file for complete search history.

(56) References Cited

U.S. PATENT DOCUMENTS

| | | | |
|---|---|---|---|
| 5,987,964 A * | 11/1999 | Miremadi | 73/31.05 |
| 6,376,124 B1 * | 4/2002 | Dodgson et al. | 429/127 |
| 6,895,805 B2 | 5/2005 | Hoagland | |
| 6,982,640 B2 | 1/2006 | Lindsay et al. | |
| 7,061,379 B2 | 6/2006 | Chen et al. | |
| 7,079,034 B2 | 7/2006 | Stilp | |
| 7,158,031 B2 | 1/2007 | Tuttle | |
| 2005/0264452 A1 * | 12/2005 | Fujishima et al. | 343/700 MS |
| 2006/0055392 A1 * | 3/2006 | Passmore et al. | 324/71.1 |
| 2006/0058697 A1 * | 3/2006 | Mochizuki et al. | 600/532 |

FOREIGN PATENT DOCUMENTS

JP    61118651 A  *  6/1986

OTHER PUBLICATIONS

Doug Cox, "Implementing Ohmmeter/Temperature Sensor", Microchip Technology, Inc. Article, AN512, Published in United States.
Peter Sorrells, "Optimizing read range in RFID systems", EDN magazine, Dec. 7, 2000, pp. 173-184, Published in United States.
Eric Sells, "World's First RFID Tagging IC with Sensor Input Targets Industrial Applications", Oct. 5, 1999, Chandler, Arizona, United States of America.

* cited by examiner

*Primary Examiner* — Bach Dinh
(74) *Attorney, Agent, or Firm* — James R. Young; Cochran Freund & Young LLC

(57) ABSTRACT

A remotely readable hydrogen detector is in the form of a tag or card that can be worn on clothing or mounted on a variety of surfaces and can be monitored from a distance for the presence of hydrogen gas. It includes a hydrogen sensor device, which changes in electrical resistivity in response to being exposed to hydrogen gas, that is incorporated into an electric detector circuit, which detects changes in resistivity of the sensor device, and, when such change in resistivity indicates the presence of some predetermined concentration of hydrogen gas, the electric circuit outputs a signal or state that indicates the presence of hydrogen to a transceiver circuit, which can transmit that information to a remote receiver or interrogator/reader via an antenna in the sensor device.

8 Claims, 4 Drawing Sheets

MONITORABLE HYDROGEN SENSOR SYSTEM

This application is a nonprovisional application of provisional application No. 60/781,419 filed Mar. 10, 2006, which is incorporated herein by reference.

BACKGROUND

The anticipated advent of large scale, broad based use of hydrogen as an energy source alternative to fossil fuels brings the anticipation of numerous and widespread hydrogen gas production, storage, transportation, and distribution facilities, any of which can develop leaks. Hydrogen gas is explosive, of course, and a buildup of hydrogen gas in any significant concentration can be dangerous. Various regulations have been developed requiring the use of hydrogen detection devices to detect the presence of hydrogen gas at one volume percent where gaseous hydrogen buildup is possible (29 C.F.R. 1910.106 (1996)) and at 0.4 volume percent for confined spaces (29 C.F.R. 1910.146 (1996)).

Detection of hydrogen gas concentrations by traditional methods, such as mass spectrometers and chromatographs, are accurate but cumbersome. To meet the need for more practical hydrogen gas detectors, attention was directed to semiconductor materials that are sensitive to hydrogen. For example, some transition metal oxides are chemochromic and change color or light absorption and reflection characteristics when exposed to hydrogen, and they were incorporated into portable, wearable detectors that undergo a visible change when in the presence of hydrogen gas. See, for example, U.S. Pat. No. 6,895,805 B2, entitled "Hydrogen Gas Indicator System," issued to W. Hoagland on May 24, 2005, which is incorporated herein in its entirety.

While such visual hydrogen gas indicator systems have certainly advanced the state of the art in useful hydrogen gas detectors, they still have to be seen to be effective, and someone has to be both present and paying attention whenever hydrogen gas is present, which can be intermittent or transient in some situations. Therefore, better monitoring systems are needed for different environments and situations.

BRIEF DESCRIPTION OF THE DRAWINGS

The accompanying drawings, which are incorporated herein and form a part of the specification, illustrate some, but not the only or exclusive, example embodiments and/or features. It is intended that the embodiments and figures disclosed herein are to be considered illustrative rather than limiting.

In the drawings.

DETAILED DESCRIPTION OF EXAMPLE EMBODIMENTS

Figure 1:
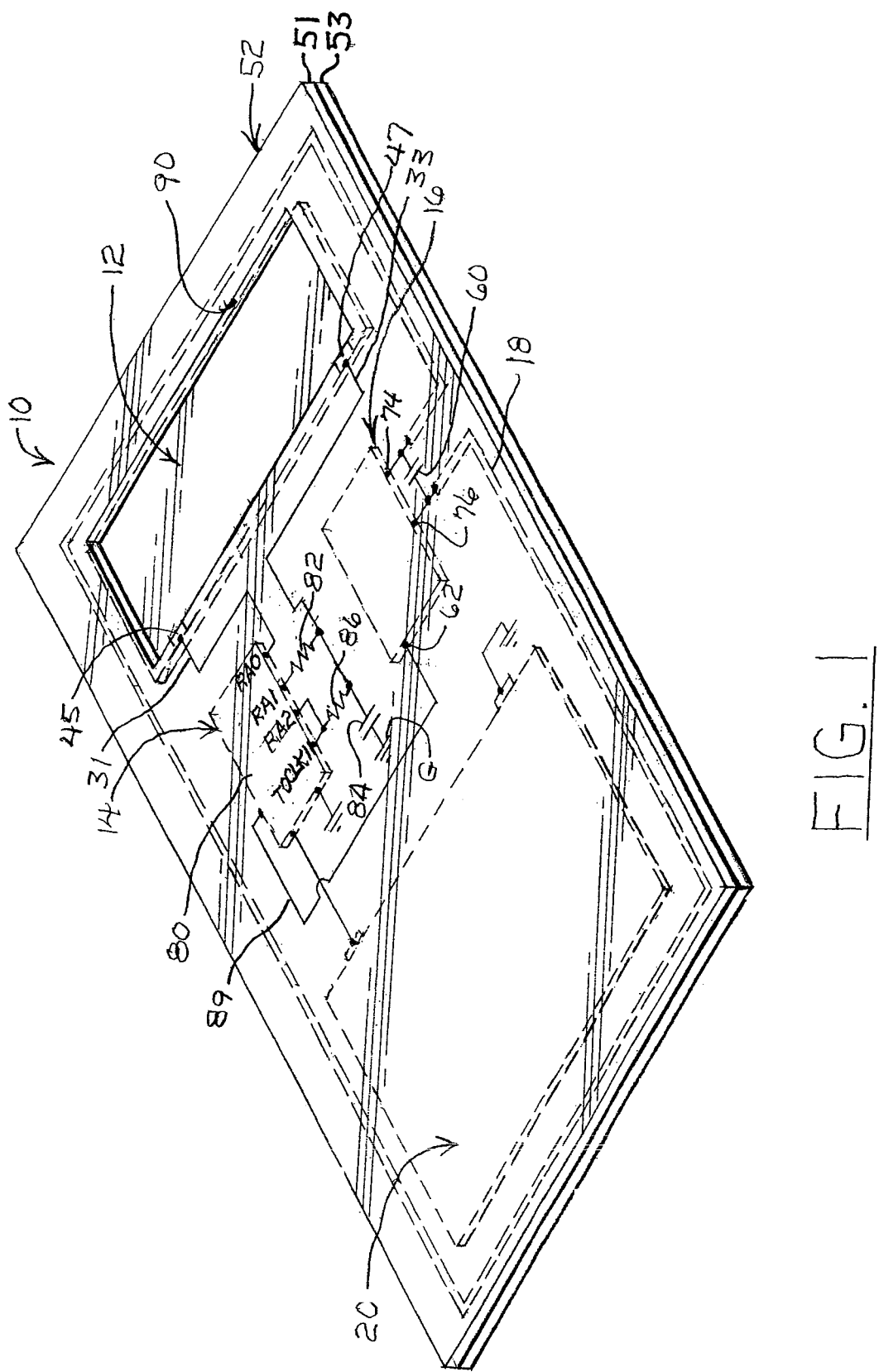
FIG. 1 is an isometric, diagrammatic view of an example embodiment of a monitorable hydrogen gas sensor tag.

An example monitorable hydrogen gas sensor tag 10 is shown diagrammatically and schematically in FIG. 1. The tag 10 can be any convenient size or shape, but it is shown as a thin card type structure 52 in FIG. 1, so it can be mounted easily on a variety of surfaces or worn on a person's clothing Essentially, the tag 10 comprises a hydrogen sensor device 12 that changes in electrical resistivity in response to being exposed to hydrogen gas. The sensor device 12 is incorporated into an electric detector circuit 14, which detects changes in resistivity of the sensor device 12, and, when such change in resistivity indicates the presence of some predetermined concentration of hydrogen gas, the electric circuit 14 outputs a signal or state that indicates the presence of hydrogen to a transceiver circuit 16, which can transmit that information to a remote receiver or interrogator/reader 30 (FIG. 2) via an antenna 18 in the tag 10. The example hydrogen gas sensor tag embodiment 10 shown in FIG. 1 is semi-passive, wherein a battery 20 is provided to power the detector circuit 14, while the transceiver circuit 16 is passive and powered by electricity induced in the antenna 18 by electromagnetic energy from an external source, e.g., from the signals 32 transmitted by the interrogator/reader transceiver 30 in FIG. 2. However, the transceiver circuit 16 in the tag 10 (FIG. 1) could easily be an active circuit, i.e., powered by the battery 20, or the detector circuit 14 could be passive and powered by electricity induced in the antenna 18.

Figure 2:
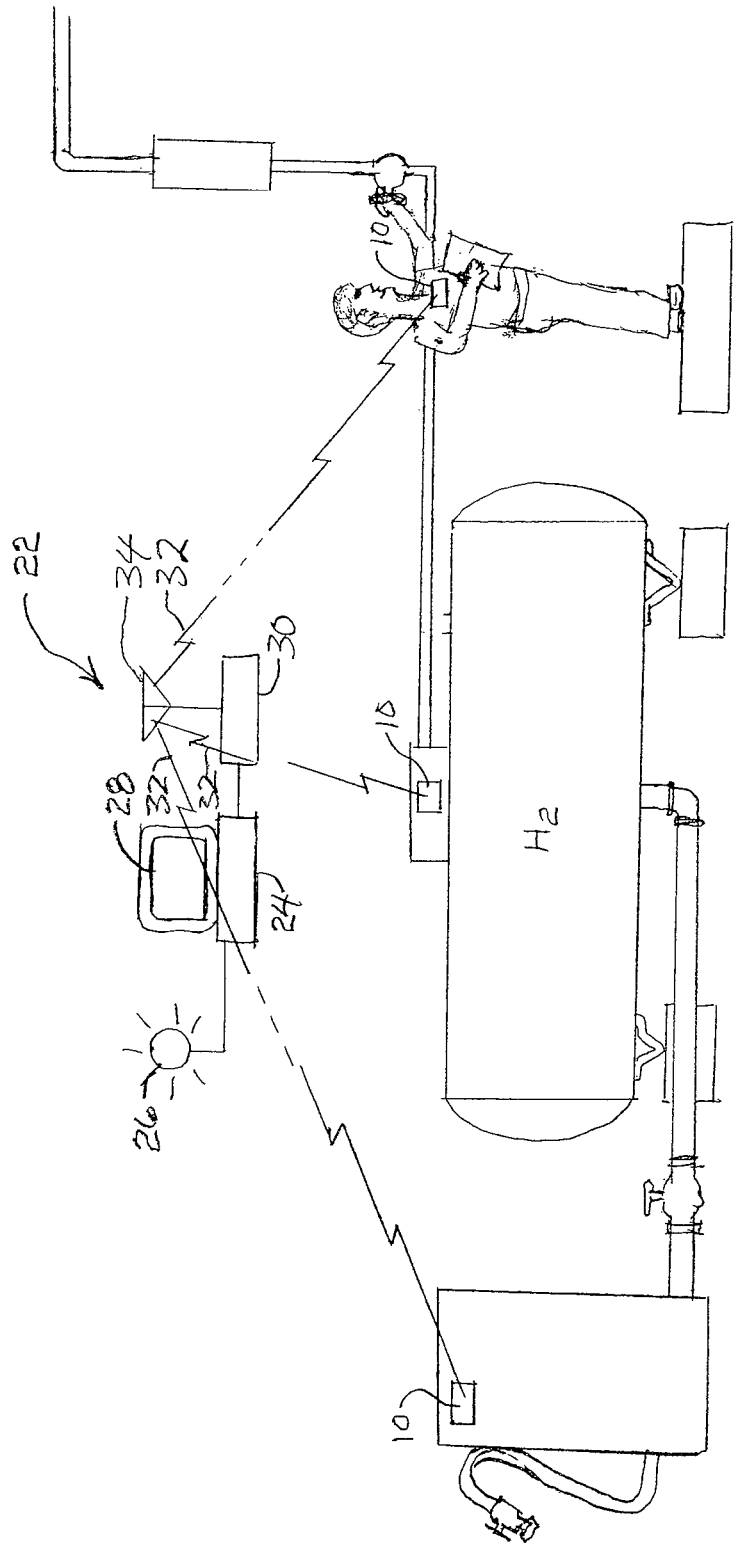
FIG. 2 is a diagrammatic view of an example environment where one or more monitorable hydrogen gas sensor tags can be deployed in conjunction with a central monitoring station.

A central station 22 shown in FIG. 2 can be used to receive information from one or more of the sensor tags 10 regarding whether any such sensor tags 10 sensed the presence of hydrogen, and such information can be processed 24, used to set off an alarm 26, recorded, stored in a memory, displayed 28, or other uses. The central station 22 can be in a fixed location, or it can be portable. The central station 22 can passively receive the information, if the tags 10 are active and transmit with their own power and at their own instigation, or it can include a transceiver 30 set up with an interrogator function to transmit signals 32 addressed to individual ones of the tags 10. Such interrogation signals 32 are received by the tags 10 and thereby instigate a responsive transmission of data from the addressed tag 10. The signals transmitted from the tag 10 can include an identification of the particular tag 10, e.g., a serial number, and present hydrogen sense status at the input 62 (FIG. 1), and/or it can include past hydrogen sense data if the tag 10 has a memory and processing capability to log sequential readings from the hydrogen sensor device 12. As mentioned above, if all or part of the tag 10 is passive or derives electric power to operate from external electromagnetic energy, it can obtain such electric power by induction from the signals 32 transmitted by the antenna 34 of the central station transceiver 30.

Figure 3:
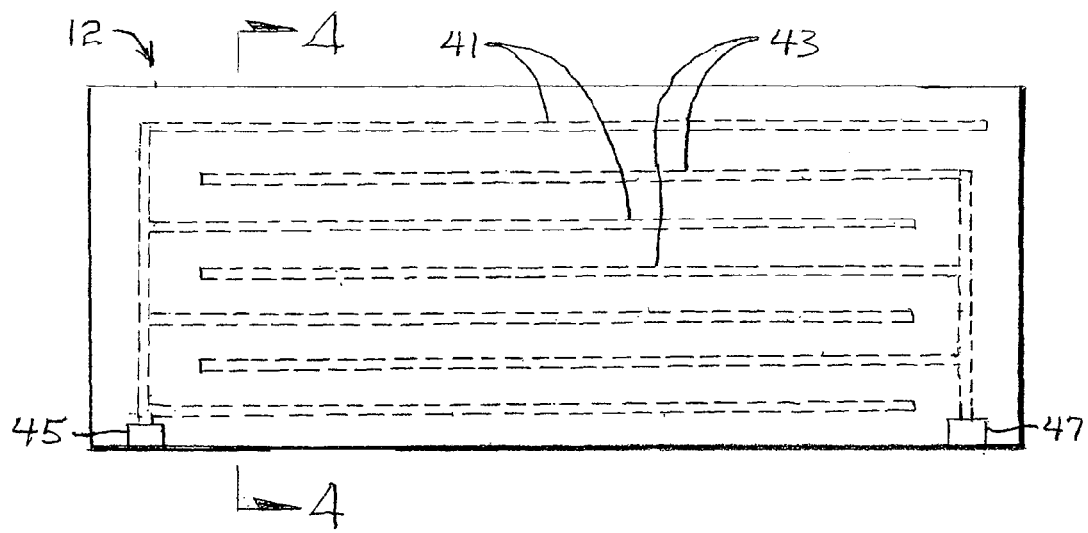
FIG. 3 is a diagrammatic plan view of an example hydrogen sensor device with interdigitated embedded conductor strips.
Figure 4:
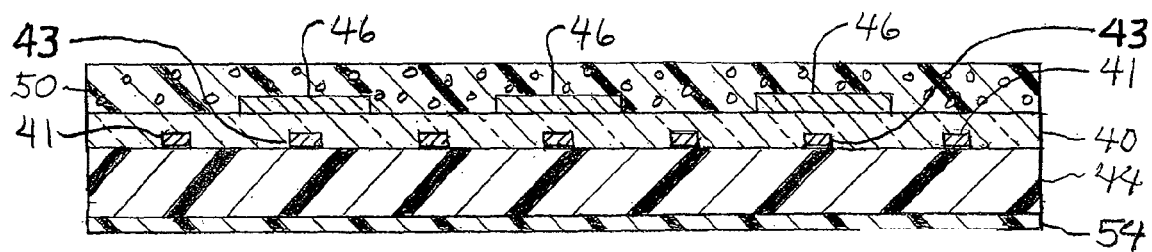
FIG. 4 is a cross-section view of the example hydrogen sensor device taken along section line 4-4 in FIG. 3.

An example hydrogen sensor device 12 is shown diagrammatically in the top plan view in FIG. 3 and in the cross-section view in FIG. 4. The example device 12 shown in FIGS. 3 and 4 is a thin film device, so the several layers are shown with exaggerated thicknesses for clarity in a manner typical and understood by persons skilled in the art. Such hydrogen sensors as described in U.S. Pat. No. 6,895,805 have variable electrical resistance or conductance in response to exposure to hydrogen. In FIG. 4, an interdigitated grid pattern of conductive contacts 41, 43, for example, aluminum, silver, gold, or other metal is deposited on the substrate 44. Then, the layer of chemo-electric material 40 is shown deposited over the electrically conductive first contact grid 41 and second contact grid 43 on the substrate 44. The chemo-electric material of layer 40 can be any of a number of transition metal oxides that change in resistivity or conductance when exposed to hydrogen, such as vanadium oxide, tungsten oxide, molybdenum oxide, yttrium oxide, palladium oxide, or combinations thereof. It is preferred, but not essential, that a catalyst layer 46 be deposited on the chemo-electric material 40 to facilitate conversion of molecular hydrogen gas ($H_2$) to atomic hydrogen, which reacts more readily with the oxygen atoms in the transition metal oxide material 40 causing a change in the oxidation state of some of the metal ions to partially reduce the metal oxide, resulting in a lower electrical resistance. Such catalyst layer 46 can comprise, for example, palladium, platinum, rhodium, nickel, combinations of these metals, and/or alloys of any of these metals with other metals, such as copper, cobalt, iridium, magnesium, calcium, barium, strontium, or others. For example, but not for limitation, the chemo-electric material 40 may be about 0.2 to 10 microns thick, and the catalyst material may be about 0.5 to 10 microns thick.

As shown in FIG. 3, the first contact grid 41 is connected to a first terminal 45, and the second contact grid 43 is connected to a second terminal 47, which facilitate electrical connection of the hydrogen sensor device 12 to the detector circuit 14, as shown by the leads 31, 33 in FIG. 1. The resistance of the chemo-electric material 40 between the first and second grids 41, 43 decreases as the hydrogen reduces the metal oxide to metal and increases as the metal is re-oxidized in the absence of hydrogen. Therefore, the presence of hydrogen can be detected by a decrease in the resistance of the chemo-electric material 40 between the first and second contact grids 41, 43.

The catalyst layer 46 is shown as intermittent or a plurality of islets on the chemo-electric material 40, because the catalyst 46 is conductive and would conduct electric current over and across the chemo-electric material 40, if it was continuous, and thereby mask and/or interfere with detection of resistance changes in the chemo-electric material.

Figure 5:
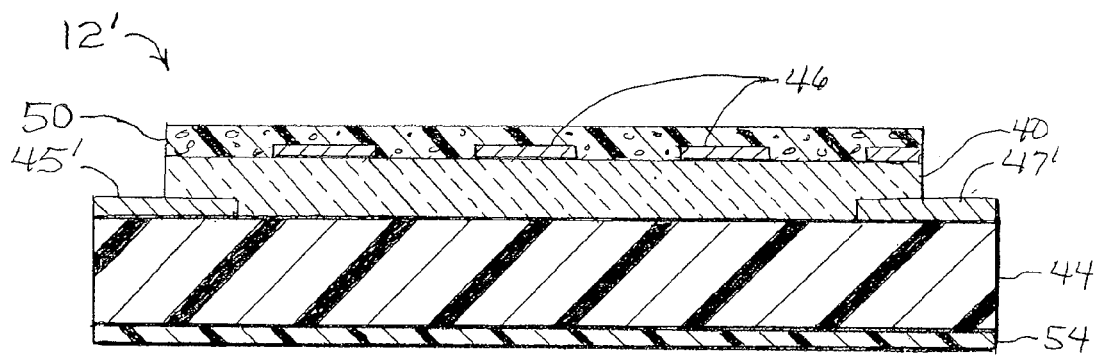
FIG. 5 is a cross-section view of another example hydrogen sensor device with contacts at opposite ends.

In another implementation of the hydrogen sensor device 12' shown in FIG. 5, there are just two electric contact pads 45', 47' on opposite ends of the substrate 44 with no grid-type contact, so in order for electricity to flow between the contacts 45', 47', it has to flow through the full length of the chemo-electric material 40, and the total resistance of the entire length of the chemo-electric material 40 between the contacts 45', 47' is detected or measured. Again, the catalyst material 46 is intermittent so that electric current does not flow through the slight thickness of chemo-electric material 40 at the ends to the catalyst 46 and then get conducted by the catalyst 46 over the chemo-electric material 40

Figure 6:
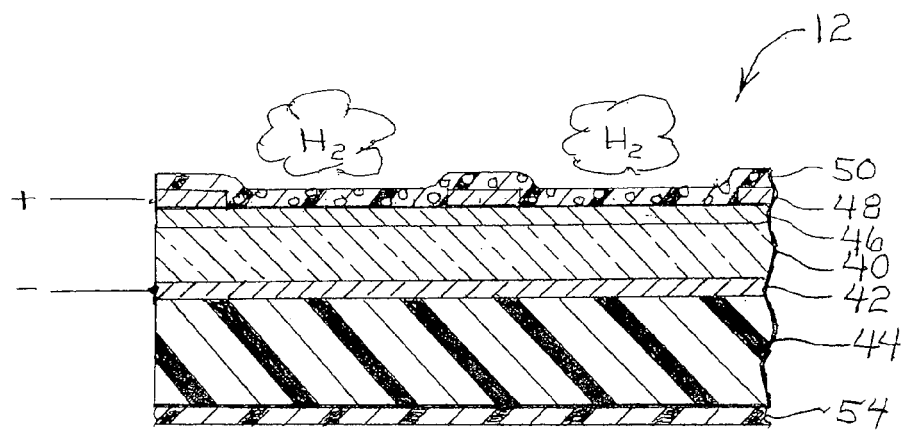
FIG. 6 is a cross-section view of still another example hydrogen sensor device.

In yet another implementation shown in FIG. 6, a first contact 42 is deposited on the substrate 44, and the chemo-electric material 40 is deposited on the first contact 42. A grid of electrically conductive material 48 is deposited on the catalyst layer 46 for the second contact so that it can conduct electricity to or from the sensor layer 40 without significantly impeding hydrogen gas from reaching the catalyst 46 and sensor layer 40. Therefore, in this implementation of FIG. 6, the catalyst layer 46 does not have to be intermittent, because the electric current would have to flow through the thickness of the chemo-electric material 40 from the first contact 42 to the top grid contact 48, regardless of the catalyst 46. Consequently, in the FIG. 6 embodiment, the resistance of the chemo-electric material 40 is detected or measured across its thickness instead of along its length or width.

In each of the hydrogen sensor implementations illustrated in FIGS. 4, 5, and 6, a molecular diffusion barrier 50, which is selectively permeable to diffusion of hydrogen gas to the exclusion of oxygen, is positioned over the catalyst 46 and grid 48 to provide an effective barrier against oxidation of the transition metal of the hydrogen sensor layer 40 in opposition to the hydrogen reduction of the transition metal oxide.

The protective molecular diffusion barrier 50 can comprise at least one thin metal film such as palladium, platinum, iridium, or other noble metals or precursors of such metals that may be used for deposition, or can comprise a polymer such as polyamides, polyacrylamides, polyacrylate, polyalkylacrylates, polystyrenes, polynitriles, polyvinyls, polyvinylchlorides, polyvinyl alcohols, polydienes, polyesters, polycarbonates, polysiloxanes, polyurethanes, polyolefins, polyimides, or heteropolymeric combinations thereof. See also U.S. Patent Publication No. 20010012539, hereby incorporated by reference herein. The molecular diffusion barrier 50 can be coupled to the catalyst material, or in those embodiments of the invention that do not employ a catalyst layer, can be coupled to the hydrogen gas sensor layer 40

The substrate 44 can be any inert material that provides sufficient support and structural integrity to the other layers of the sensor device 12, for example, plastic, glass, metal, paper, etc. It can be a part of the card or housing structure 52 of the hydrogen sensor tag 10, or it can be a separate substrate so that the sensor device 12 can be fabricated separately and mounted as a component in the card or housing 52 of the tag 10.

For further examples, the substrate 44 can be configured as blanks cut from substantially rigid sheet material; or the substrate material 44 can be a flexibly conformable material that can conformably mate with other objects that carry, interact with, or are employed in the distribution of hydrogen gas, such as pipes, containers, pumps, or the like; or the substrate material 44 can be rigidly configured material that makes up a component or element that is assembled as part of a construct to carry, interact with, or is employed in the distribution of hydrogen gas; or the substrate material 44 can be a material installed to or used within an enclosed area in which hydrogen gas can collect; or the substrate material 44 can be a material used to make clothing, outerwear, or accessories worn by individuals that work or utilize spaces, areas, or enclosures that can potentially bring them into contact with hydrogen gas; or the substrate material can be configured to fit into a container holder, sampler, badge, or other construct in manner that the hydrogen gas indicator can interact with the gaseous environment.

In some embodiments of the invention, the substrate material 44 can further have an optional adhesive layer 54 (see FIGS. 4-6) on at least a portion of the surface of the substrate material 44, such that the substrate material acts, as but one example, similar to adhesive tape. The invention may also further comprise a disposable material (not shown) to which the substrate material 44 having an adhesive layer 54 on at least a portion of the surface can be separately or peelably joined, such as decals, adhesive strips, adhesive dots, or the like. For example, the optional adhesive material 54 in FIG. 4 can be used to mount the sensor device 12 in the card or housing 52 (FIG. 1) of the sensor tag 10.

The detector circuit 14 and transceiver circuit 16 can be constructed and configured in many different ways to accomplish some or all of the functions described herein, and the components and circuits shown in FIG. 1 are just examples of such circuits. For example, the transceiver circuit 16 can be provided by any of a number of radio frequency identification (RFID) circuits and/or chips that are commercially available.

In one example implementation, a passive "microID" (trademark) RFID chip manufactured by Microchip Technology, Inc., of Chandler, Ariz., e.g., part no. MCRF250, with anti-collision capability for multiple object identification in the same reader field, as illustrated in FIG. 2, or part no. MCRF202 that, in addition to transmitting its unique ID code, is designed to detect the logic state or switch position of an external device, e.g., at input 62 in FIG. 1, and alter its ID data transmissions based on that sensor input, or part no. MCRF355 for an even lower power consumption and longer read range can be used for the transceiver circuit 16 in FIG. 1. Detailed design and setup guidelines for these microID® RFID chips are available from Microchip Technology, Inc., including, but not limited to "microID® 125 kHz RFID System Design Guide," document DS51115F, 2004, which is incorporated herein by reference and can be accessed on the website of Microchip Technology, Inc.

Essentially, the antenna loop 18 and capacitor 60 (FIG. 1) form an LC modulating circuit that generate induced AC electric power when an RF field or carrier wave from the reader/interrogator transceiver 30 (FIG. 2) passes through the antenna loop 18 (FIG. 1), which powers and wakes up the RFID chip 16. The RFID chip 16 includes a rectifier circuit that rectifies the voltage on the external LC antenna circuit to produce the operating voltage Vcc, and it clamps any excessive voltage on the circuit to a safe level to prevent damage to the RFID chip 16. The rectifier circuit 64 and operating voltage output Vcc are depicted diagrammatically in the function block diagram of the RFID chip 16 in FIG. 7.

The RFID chip 18 checks the logic state on the input 62 (FIGS. 1 and 7) from the detector circuit 14 (FIG. 1), which indicates whether the preset threshold concentration level of hydrogen gas is detected by the hydrogen sensor device 12 and detector circuit 14, and then it transmits that information along with the particular RFID chip identification information, e.g., serial number, which is stored in a memory 70 in the RFID chip 16 (FIG. 7), back to the reader/interrogator transceiver 30 (FIG. 2). The RFID chip 18 has a clock generator function 66 that generates a clock based on the carrier frequency from the interrogator/reader transceiver 30. This clock is used to drive all timing in the RFID chip 16, including the baud rate and modulation rate used in the modulator control 68.

Figure 7:
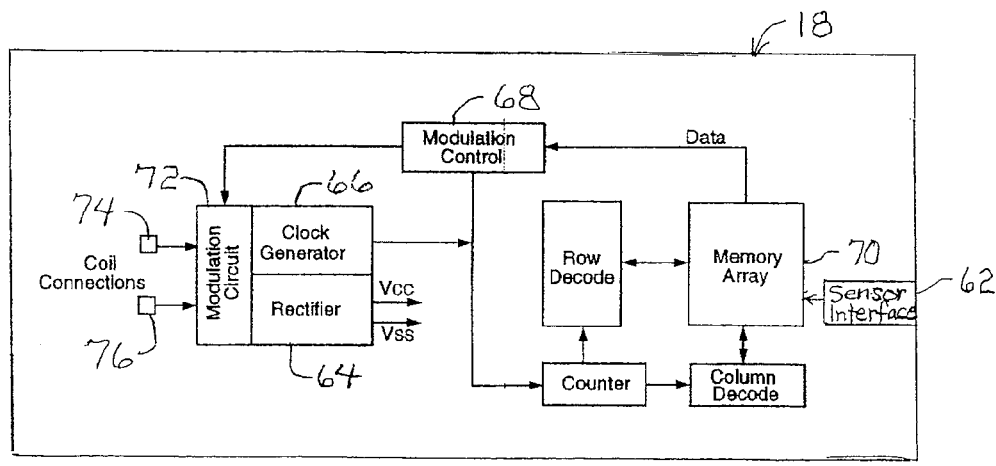
FIG. 7 is a function block diagram of the example transceiver circuit on the tag.

The data is transmitted by the RFID chip 16 by backscatter back to the interrogator/reader transceiver 30 (FIG. 2), i.e., by using the same RF carrier signal as was transmitted by the interrogator/reader transceiver 30. In other words, the RFID chip 16 sends the encoded data to the interrogator/reader transceiver 30 by AM modulating the coil voltage across the tuned LC circuit 18, 60 (FIG. 1). The modulation control 68 (FIG. 7) controls a modulation circuit 72 that includes a transistor between the two antenna 18 (FIG. 1) connections 74, 76 (FIG. 7). The modulation transistor in circuit 72 damps or undamps the coil voltage when it sends data. The variation of coil voltage controlled by the modulation transistor results in a perturbation of voltage in the interrogator/reader antenna coil 34, which can be monitored to reconstruct the data transmitted.

Again, the microID® RFID chips, made by Microchip Technology, Inc., are only examples of suitable transceiver circuits 18. Another example is the VarioSens® RFID chip, made by KSW Microtec AG of Dresden, Germany, which can receive, process, and transmit multiple value sensor input, i.e., multiple hydrogen concentration levels when used with a hydrogen sensor device 16 as explained above, if the hydrogen sensor device 16 is sensitive enough to make such multiple levels meaningful.

Likewise, the detector circuit 14 can be implemented to output a signal indicative of a hydrogen concentration in a number of ways, since the operative characteristic to be measured is resistance in the sensor device 16 that varies as a function of hydrogen concentration in the atmosphere adjacent the sensor device 12. For example, a wheatstone bridge circuit combined with a reference voltage and comparator similar to that shown in U.S. Pat. No. 7,076,920, issued to Holcombe et al., could be used to measure varying resistance in the sensor and that patent is incorporated herein by reference. However, in the example implementation shown in FIG. 1, the detection circuit 14 comprises a microcontroller 80 and associated external RC circuit setup for detecting and measuring the change in resistivity of the chemo-electric material 40 due to the presence of hydrogen.

In this example in FIG. 1, the microcontroller 80 may be, for example, one of the PIC16C5X series programmable microcontrollers manufactured by Microchip Technology, Inc., of Chandler, Ariz., such as the PIC16C54. The hydrogen sensor device 12 is connected by leads 31, 33 into an RC circuit that has a capacitor 84 in series between the hydrogen sensor device 12 and ground G. This capacitive charging circuit is used to convert resistance to time, which is measured with the microcontroller 80. Essentially, the microprocessor 80 applies a voltage to charge the capacitor 84, for example, through the parallel resistor 86 and/or the hydrogen sensor device 12. When the capacitor 84 is charged to a desired voltage, the charge is allowed to leak off through the hydrogen sensor device 12. If hydrogen is present, the resistance of the chemo-electric material 40 of the sensor device 12 is less, as explained above, so the charge drains out of the capacitor 84 in less time. On the other hand, if there is no hydrogen present, then the resistance of the chemo-electric material 40 is greater, and it takes more time to drain the charge from the capacitor 84. Therefore, the time required to drain the capacitor 84 from a trigger or threshold voltage level to a lower reference value is indicative of the resistivity of the sensor device 12, thus also of the presence or absence of hydrogen. The microprocessor 80 can have a memory and lookup table, and it can be programmed to check the capacitance drain time against the values in the lookup table. When the drain time is as low as a present pre-set time that has been determined or calibrated to mean a threshold hydrogen concentration, the microprocessor 80 sets or resets an output state on lead 89 to the input 62 of the RFID transceiver circuit 16, which means the presence of hydrogen has been detected. The RFID transceiver 16 then transmits that information to the interrogator/reader transceiver 30, as explained above. If the RFID transceiver 16 is passive, it will transmit that information when interrogated. If it is active, i.e., powered by the battery 20, it can be programmed to initiate the transmission of the information on its own. Active RFID transceivers can also continuously or periodically detect and log the hydrogen concentration status or information over time and transmit that information either on its own instigation or upon being interrogated. Either passive or active RFID transceiver implementations can be used.

As mentioned above, there are other ways of detecting resistivity of the hydrogen sensor device 12 and to correlate such resistivity to hydrogen concentration and transmit that information, and there are many microcontrollers that can perform those functions. Also, while the example implementation in FIG. 1 has been shown and described with separate chips for the RFID circuit 16 and the detector circuit 14, those and other functions can be combined together in one RFID microprocessor chip or separated into more individual components, as is understood by persons skilled in the art. Also, other communication modes, such as WiFi, VHF, UHF, or FM can be used to communicate the condition or state of the hydrogen sensor device 12 to a central station or other device to indicate a hydrogen gas leak or dangerous concentration remotely.

In another example slightly different implementation, a calibration feature can be included that can compensate for first order errors, such as offset, gain, capacitance inaccuracy or variation, power supply voltage, and temperature variations. In this calibration technique, which is adapted from a paper authored by Doug Cox, entitled "Implementing Ohmmeter/Temperature Sensor," published by Microchip Technology, Inc., in 1997 (Document DS00512E), which is incorporated by reference and is available on the website of Microchip Technology, Inc., a reference voltage is applied first to a calibration resistor 82, which is in electrical parallel to the hydrogen sensor device 12, and the capacitor C is charged up until a threshold in the microprocessor 80 trips. This step generates a calibration time value that is used to calibrate out circuit errors. The capacitor 84 is then discharged. After the capacitor 84 is discharged, the voltage is applied again, but to the hydrogen sensor device 12. The time to charge the capacitor 84 to the trip threshold is measured and compared to the calibration time value to determine the actual resistance by the relationship:

$$R_{12} = \frac{T_{12}}{T_{82}} \times R_{82},$$

where $R_{12}$ is the resistance of the hydrogen sensor device 12, $R_{82}$ is the known resistance of the calibration resistor 82, $T_{12}$ is the time to charge the capacitor 84 to the threshold through the hydrogen sensor device 12, and $T_{82}$ is the time to charge the capacitor 84 to the threshold through the calibration resistor 82. The value of $R_{12}$ is then used with a lookup table by the microprocessor 80 to determine the hydrogen concentration.

The battery 20 can be any of a number of thin film batteries available commercially that are well known in the art. For example, such thin film lithium batteries are available from Varta Microbattery, Inc., White Plains, N.Y.

As mentioned above, the example hydrogen gas sensor tag 10 in FIG. 1 is a laminate card structure 52 comprised of a top sheet 51 united with a bottom sheet 53 in juxtaposed contact with each other. Essentially, the components 12 (hydrogen sensor), 14 (detector circuit), 16 (transceiver circuit), 18 (antenna), and 20 (battery) are mounted in coplanar relation to each other on the bottom sheet 53 of plastic or other suitable material and then covered or sandwiched by the top sheet 51 of similar material. A window 90 in the top sheet 51 exposes the hydrogen sensor 12 to the environment, so it can be exposed to any hydrogen gas in the environment. However, any other structure or materials or configuration to mount these components or other components as explained above can be used to detect hydrogen gas concentration and transmit that information to another device for notification, alarm, storage, display, or other use would be satisfactory.

While a number of exemplary aspects and embodiments have been discussed above, those of skill in the art will recognize certain modifications, permutations, additions, and sub-combinations thereof. It is therefore intended that the following appended claims and claims hereafter introduced are interpreted to include all such modifications, permutations, additions, and sub-combinations as are within their true spirit and scope. The words "comprise," "comprises," "comprising," "composed," "composes," "composing," "include," "including" and "includes" when used in this specification, including the claims, are intended to specify the presence of stated features, integers, components, or steps, but they do not preclude the presence or addition of one or more other features, integers, components, steps, or groups thereof.

The embodiments of the invention in which an exclusive property or privilege is claimed are defined as follows:

1. A hydrogen detector apparatus, comprising:
    a thin card structure comprising a top sheet with a window opening united with a bottom sheet;
    a hydrogen sensor device mounted and sandwiched between the top sheet and the bottom sheet of the thin card structure in a position that exposes the hydrogen gas sensor device to the window opening in the top sheet, said hydrogen gas sensor device comprising a thin layer of chemo-electric material that varies in electrical resistivity in response to exposure to hydrogen, at least two electrically conductive contacts in physical contact with the thin layer of chemo-electric material and spaced apart from each other by the intervening thin layer of chemo-electric material, and a catalyst layer disposed on a surface of the intervening thin layer of chemo-electric material;
    a detector circuit mounted and sandwiched between the top sheet and the bottom sheet and connected to the at least two electrically conductive contacts of the hydrogen sensor device in a manner that is capable of applying a voltage across the thin layer of chemo-electric material between the at least two electrically conductive contacts and detecting resistivity of the thin layer of chemo-electric material between the at least two electrically conductive contacts that is indicative of the thin layer of chemo-electric material being exposed to hydrogen and of generating a signal in response to such detection, said detector circuit comprising an RC circuit that includes a capacitor in series between the hydrogen sensor device and a ground to convert resistance in the hydrogen sensor device to time, and a microcontroller connected to the RC circuit programmed to measure a time required to discharge the capacitor through the hydrogen sensor from a threshold voltage level to a lower reference value and to compare such measured time to a time value that is indicative of a hydrogen concentration, and to generate the signal; and
    a transceiver circuit mounted and sandwiched between the top sheet and the bottom sheet, wherein said transceiver circuit is connected electrically to the detector circuit to receive the signal generated by the detector circuit and includes a transmitter which transmits information indicating presence of hydrogen at the hydrogen sensor device to a remote receiver in response to the signal generated by the detector circuit.

2. The hydrogen detector apparatus of claim 1, wherein the catalyst layer includes an intermittent conductive catalyst spaced apart enough so that electricity flowing between the at least two contacts has to flow through the chemo-electric material instead of through the conductive catalyst.

3. The hydrogen detector apparatus of claim 1, further comprising:
    a battery mounted and sandwiched between the top sheet and the bottom sheet of the thin card structure, said battery being connected electrically to the detector circuit.

4. The hydrogen detector apparatus of claim 1, wherein the hydrogen gas sensor device, the detector circuit, and the transceiver circuit are mounted in adjacent, coplanar relation to each other sandwiched between the top sheet and the bottom sheet of the thin card structure.

5. The hydrogen detector apparatus of claim 4, wherein the transceiver circuit includes an antenna extending in coplanar relation to the hydrogen gas sensor device, the detector circuit and the transceiver circuit are mounted adjacent to each other between the bottom sheet and the top sheet of the thin card structure.

6. The hydrogen detector apparatus of claim 1, wherein the hydrogen gas sensor device includes at least two electrically conductive contacts in contact with a first surface of the thin layer of chemo-electric material and the catalyst layer in intermittent islets on a second surface of the thin layer of chemo-electric material that is opposite the first surface.

7. The hydrogen detector apparatus of claim 6, wherein the at least two electrically conductive contacts extend in interdigitated relation to each other in contact with the first surface of the thin layer of chemo-electric material.

8. The hydrogen detector apparatus of claim 1, wherein a first of the at least two electrically conductive contacts is in physical and electrical contact with one surface of the thin layer of chemo-electric material, the catalyst layer on another surface of the thin layer of chemo-electric material that is opposite said first electrically conductive contact, and a second of the at least two electrically conductive contacts is formed as a grid on the catalyst layer such that the first and second electrically conductive contacts are spaced apart from each other by the thin layer of chemo-electric material so that electricity flowing between the first and second electrically conductive contacts has to flow through the thin layer of chemo-electric material and such that the second electrically conductive contact is not an impediment to hydrogen gas flow from the window opening in the top sheet to the catalyst layer and the thin layer of chemo-electric material.

* * * * *